United States Patent [19]

Piau

[11] Patent Number: 5,502,394
[45] Date of Patent: Mar. 26, 1996

[54] COMPACT, PORTABLE DEVICE FOR MEASURING THE REFLECTION COEFFICIENT OF A STRUCTURE EXPOSED TO MICROWAVE RADIATION

[75] Inventor: Gérard P. Piau, Puteaux, France

[73] Assignee: Aerospatiale Société Nationale Industrielle, France

[21] Appl. No.: 326,530

[22] Filed: Oct. 20, 1994

[30] Foreign Application Priority Data

Oct. 25, 1993 [FR] France ................... 93 12685

[51] Int. Cl.⁶ ........................... G01R 27/04
[52] U.S. Cl. ........................... 324/646; 324/642
[58] Field of Search ................... 324/637, 642, 324/646, 66, 67, 639

[56] References Cited

U.S. PATENT DOCUMENTS

| | | | |
|---|---|---|---|
| 3,025,463 | 3/1962 | Fairborn | 324/642 |
| 3,562,642 | 2/1971 | Hoshschild | 324/642 |
| 3,936,736 | 2/1976 | Ray | 324/642 |
| 4,097,796 | 6/1978 | Lunden | 324/642 |
| 5,233,306 | 8/1993 | Misra | 324/646 X |
| 5,371,505 | 12/1994 | Michaels | 324/639 X |
| 5,384,543 | 1/1995 | Bible et al. | 324/637 X |

FOREIGN PATENT DOCUMENTS

WO91/10899 7/1991 WIPO.

*Primary Examiner*—Kenneth A. Wieder
*Assistant Examiner*—Diep Do

[57] ABSTRACT

In order to measure the amplitude and the phase of the reflection coefficient of a structure (S) such as a radar protection radome, particularly following a repair, a measuring device is proposed, whereof a portable part (10) makes it possible to transform the microwave measuring and reference signals into low frequency signals. These low frequency signals are then transferred by flexible cables (16, 17) to a calculating part (12, 14) without it being possible to create phase distortions by twisting of the cable. The signals are transformed by giving the portable part, in addition to the main microwave generator (18), a second microwave generator (32), whose frequency ($f_2$) differs from that ($f_1$) of the main generator by a given low frequency ($f_0$). Microwave mixers (38, 42) use the radiation emitted by the second generator (32) in order to give the measuring signal and the reference signal, initially at the frequency ($f_1$), the low frequency ($f_0$).

7 Claims, 1 Drawing Sheet

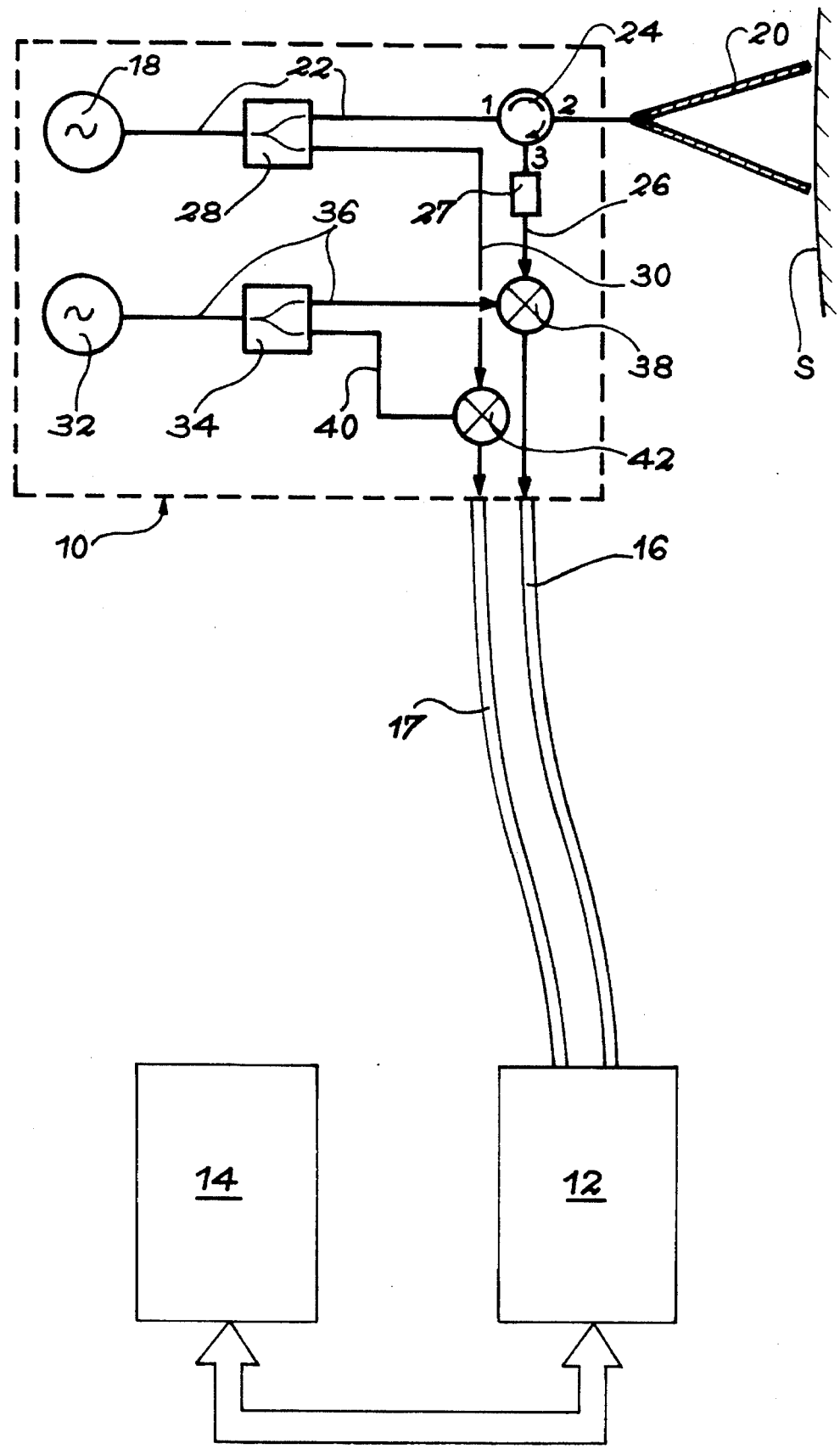

COMPACT, PORTABLE DEVICE FOR MEASURING THE REFLECTION COEFFICIENT OF A STRUCTURE EXPOSED TO MICROWAVE RADIATION

BACKGROUND OF THE INVENTION

The invention relates to a device making it possible to measure the reflection coefficient of a structure such as a non-metallic, monolithic or composite structure, when the latter is exposed to microwave radiation.

Such a measuring device can in particular be used for checking the radio transparency of a structure such as that of a radome protecting a radar carried on an aircraft. Other applications of said device can be envisaged without passing outside the scope of the invention.

Radomes protecting radars equipping aircraft can be subject, both on the ground and in flight, to impacts liable to damage them. Thus, they can be struck by an engine when on the ground. They can also be struck by birds or lightning when the aircraft is flying.

Damaged radomes undergo repairs in order to restore their integrity. However, even though such repairs give the radomes their mechanical integrity, they sometimes lead to a modification of the transparency to radiation emitted by the radar in the repaired area. This modification can lead to an error concerning the position and/or distance from an obstacle or in the extreme case the non-detection of an obstacle.

It is therefore desirable to have a measuring device making it possible to control the radiotransparency of radomes after the latter have undergone repairs. Such a device could also be used for controlling the radiotransparency of new radomes during their manufacture.

In order to carry out such measurements, it is known to use an anechoic chamber into which the radome is introduced. However, this is a cumbersome and costly procedure, which does not make it possible to carry out the control or inspection in the workshop or on site.

Measuring devices used in the laboratory are also known, which are called vector network analyzers, which make it possible to simultaneously determine the amplitude and phase of the reflection coefficient of a structure exposed to microwave radiation. These devices, which operate in a wide frequency range, are heavy (15 to 20 kg) and cumbersome. They are therefore relatively unsuitable for use in the workshop or on site.

In addition, due to the large overall dimensions and weight of such a device, the microwave applicator used for emitting the microwave radiation to the structure to be controlled and for receiving the waves reflected by said structure, must be separate from the remainder of the device and connected thereto by a microwave lead which is as flexible as possible and which has an adequate length to make it possible to displace the microwave applicator over the entire surface of the structure to be controlled. However, said microwave lead is a source of problems, because it has at its ends fragile connectors and any twisting of said leads to distortions to the phase of the microwave signals which it transmits. Therefore the measurements performed can be subject to sometimes significant errors with respect to the phase of the signal.

U.S. Pat. No. 3,025,463 to Luomaetal describes a device making it possible to measure the amplitude and phase of the reflection coefficient of a structure to be controlled.

In the first embodiment described, it is a portable device incorporating a single high frequency generator directly connected by a waveguide to a high frequency applicator. In the waveguide, part of the incident wave and part of the reflected wave are sampled in order to be passed to a mixer, which calculates the difference thereof. Manual regulating systems make it possible to modify the amplitude of the fraction of the incident wave directed to the mixer and the phase of the fraction of the reflected wave directed to said same mixer. These settings are carried out so as to cancel out the signal received by the detector. The corresponding values then represent the amplitude and phase of the reflection coefficient of the structure. Although this device is completely portable, its utilization is particularly long and clearly inappropriate for industrial control and inspection purposes.

In the second embodiment described in the Luoma reference, the measuring device is equipped with an additional circuit making it possible to automatically cancel out the signal received by the detector. However, it is a much heavier and more voluminous device, which has a fixed part and a mobile part interconnected by a cable. This cable carries both electric signals and microwave radiations, leading to the disadvantages due to the presence of a flexible, relatively long microwave lead already referred to in the case of vector network analyzers.

SUMMARY OF THE INVENTION

The invention specifically relates to a device making it possible to measure both the amplitude and the phase of the reflection coefficient of a structure exposed to microwave radiation, whilst avoiding any error with respect to the phase and without prejudicing the ease of handling and use for industrial purposes.

According to the invention, this result is obtained by means of a device for measuring the reflection coefficient of a structure exposed to microwave radiation comprising:

a first microwave radiation generator emitting at a first given frequency, at least one microwave applicator which can be plated to the structure, a rigid microwave transmission line connecting the generator to the applicator, means for measuring the amplitude and phase of the reflection coefficient, branching means placed in the transmission line and connecting the latter to the measuring means, characterized in that it also comprises:

a second microwave radiation generator emitting at a second given frequency, which differs from the first fixed frequency by a given low frequency, first mixer means for establishing a reference signal at said low frequency, on the basis of the signals from the first and second generators, second mixer means for establishing a measuring signal at said low frequency, on the basis of signals from the branching means and the second generator, and in that the first and second generators, the microwave applicator, the first and second mixer means, the branching means and the microwave transmission line form a portable device connected to the measuring means by flexible, low frequency cables.

The means installed on the portable device makes it possible to transform the microwave reference signal from the first microwave radiation generator and the microwave measuring signal reflected by the structure to be controlled into low frequency signals. These low frequency signals are transmitted to the measuring means by two low frequency, flexible cables, whose possible twisting has no effect on the precision of the measurements and in particular on the phase of the measured signal, no matter what the length of the cables. Thus, reliable, reproducible measurements are obtained.

Moreover, the means installed on the portable device has a light weight and small overall dimensions, so that said portable device is easy to handle and consequently aids industrial use of the measuring device, particularly within the framework of inspecting new radomes or those which have undergone repairs.

In a preferred embodiment of the invention, the portable device also comprises:

a first power divider placed on the microwave transmission line upstream of the branching means, sampling a given power fraction of the microwave radiation emitted by the first generator in order to transmit it to the first mixer means and a second power divider placed on a second microwave transmission line connecting the second generator to the second mixer means and sampling the same given power fraction of the microwave radiation emitted by the second generator in order to transmit it to the first mixer means.

Preferably, the power dividers sample half the power of the microwave radiations emitted by the first and second generators.

In the preferred embodiment of the invention, the branching means comprises a circulator ensuring the transmission to the microwave applicator of the microwave radiation coming from the first generator and the transmission to the second mixer means of the microwave radiation reflected by the structure and intercepted by the microwave applicator, and preventing any other transmission.

In order to improve the compactness of the portable device, the microwave applicator is preferably directly connected to the branching means.

Advantageously, the measuring means comprises detecting means, which determines the amplitude and phase of the reflection coefficient. These detection means can be constituted by a vector voltmeter or by an amplitude and phase detector, commonly called an I/Q detector. Moreover, said measuring means comprises means for the recording and exploiting of the amplitude and phase determined by the detection means.

BRIEF DESCRIPTION OF THE INVENTION

The invention is described in greater detail hereinafter relative to a non-limitative embodiment and the single drawing diagrammatically showing a device according to the invention able to measure the reflection coefficient of a structure exposed to microwave radiation.

DETAILED DESCRIPTION OF THE INVENTION

As is diagrammatically illustrated by the drawing, the measuring device according to the invention comprises a portable device 10, as well as measuring means including detection means 12 such as a vector voltmeter or I/Q detector, as well as means 14 for recording and exploiting information supplied by the detection means 12. The portable device 10 is connected to the detection means 12 by flexible, low frequency cables 16, 17, which can have a random length.

The portable device 10 includes a first microwave radiation generator 18 e.g. constituted by a microwave oscillator able to emit microwave radiation. The frequency $f_1$ of said radiation is dependent on the structure S which is to be controlled. In the case where said structure is constituted by a radar protection radome, said frequency $f_1$ is advantageously the frequency of the radar, e.g. a frequency of approximately 9 to 10 GHz.

The first microwave radiation generator 18 is connected by a microwave transmission line 22 to a microwave applicator e.g. constituted by a microwave horn 20 mounted on the portable device 10. The microwave transmission line 22 is constituted by a very short waveguide or a rigid coaxial line.

On the microwave transmission line 22, the microwave radiation is transmitted from the first generator 18 to the microwave horn 20 through branching means e.g. constituted by a circulator 24.

More specifically, the circulator 24 makes it possible to transmit all at its output 2, on which is connected the microwave horn 20, the microwave radiation entering at its input 1, to which is connected the first generator 18 and transmit all at its output 3, to which is connected a microwave measuring line 26, the microwave radiation reaching it by the output 2, whilst preventing any other transmission. The microwave measuring line 26 is equipped with a microwave attenuator 27. The microwave radiation reflected by the structure S and intercepted by the microwave horn 20 forms a measuring signal, which is therefore reflected by the circulator 24 into the microwave measuring line 26 and microwave attenuator 27.

In order to reduce to the greatest possible extent the length of the microwave transmission line 22, the microwave horn 20 is directly connected to the circulator 24.

A first power divider 28 is also placed on the microwave transmission line 22 between the first generator 18 and the circulator 24. This power divider 28 makes it possible to sample a fraction of the power of the microwave radiation emitted by the first generator 18 in order to direct it into a microwave reference line 30. This fraction of the microwave radiation emitted by the generator 18 and directed to the microwave reference line 30 constitutes a reference signal with which can be compared the measuring signal intercepted by the microwave horn 20 and directed to the microwave measuring line 26 by the circulator 24. Advantageously, the power divider 28 samples half the power of the microwave radiation emitted by the first generator 18 in order to direct it to the microwave reference line 30.

According to the invention, the portable device 10 also has means making it possible to transform into low frequency signals the microwave signals forming the measuring signal admitted into the microwave branching line 26 and the reference signal admitted to the microwave line 30. More specifically, said means makes it possible to transform the microwave measuring signal and the microwave reference signal into signals, whose frequency $f_0$ is sufficiently low that they can be transmitted by the flexible cables 16, 17 without any risk of distortion of their phase due to twisting of said cable. For this purpose, a frequency $f_0$ between 60 and 200 MHz is satisfactory.

The aforementioned means ensuring the transformation of the measuring signal and the reference signal into low frequency signals, comprises a second microwave radiation generator 32 also constituted by a microwave oscillator mounted in the portable device 10. Said second generator 32 emits a microwave radiation at a given frequency $f_2$ equal to the frequency $f_1$ of the radiation emitted by the first generator 18, increased or decreased by a given low frequency $f_0$, corresponding to the low frequency of the signals which it is wished to transmit by the flexible cables 16, 17. The frequency $f_2$ of the microwave radiation emitted by the second generator 32 is therefore $f_1 \pm f_0$.

The microwave radiation emitted by the second generator 32 is carried by a second microwave transmission line 36. A second power divider 34, placed in said second transmission line 36, samples a given power fraction identical to that sampled by the first power divider 28 of the microwave radiation emitted by the second generator 32. Therefore said power fraction is advantageously equal to half the power of the radiation emitted by the second generator 32.

The microwave measuring line 26 and the second microwave transmission line 36 are connected to first microwave mixer means 38 within the portable device 10. In order to optimize the operation of the first mixer means 38, the microwave line 26 is equipped with the microwave attenuator 27. Therefore said first mixer means 38 receive the microwave measuring signal at frequency $f_1$ from the microwave measuring line 26 and the microwave signal at frequency $f_2$ from the microwave line 36. At its output the mixer means 38 restores a signal, whose amplitude and phase are proportional to the measuring signal, but whose frequency is equal to the difference between the frequencies $f_2$ and $f_1$. The measuring signal from the mixer means 38 is therefore a signal at the frequency $f_0$, i.e. a low frequency signal. Consequently said low frequency signal can be transmitted to the detection means 22 by the flexible cable 16 without any risk of phase error due to the twisting of said cable, even if the latter has a considerable length.

In comparable manner, the microwave reference line 30 and the microwave line 40 from the branching means 34 are connected to second microwave mixer means 42 within the portable device 10. This mixer means 42 has the same characteristics as the mixer means 38. Thus, at its output it restores a reference signal, whose amplitude and phase are proportional to the microwave reference signal flowing in the microwave reference line 30, but whose frequency is equal to $f_0$. The reference signal leaving the mixer means 42 is consequently a low frequency signal, which can also be passed to the detection means 12 by the flexible cable 17 without any risk of phase error, despite any twisting of the cable.

The detection means 12 receiving the low frequency measuring and reference signals transmitted by the flexible cables 16 and 17 determines, on the basis of these signals and in known manner, the amplitude and phase of the reflection coefficient of the structure S. When the detection means 12 is constituted by a vector voltmeter, the latter advantageously has a screen on which are displayed the thus determined amplitude and phase values.

The means 14 for recording and exploiting values determined by the detection means 12 comprises a computer, which records the measured amplitude and phase values. By means of appropriate software, it also ensures the processing and interpretation of said values in order to present them in an easily exploitable form.

During the use of the device according to the invention, there is successively a calibration of the apparatus, a first measurement with a reflector placed on the opposite face of the structure to be controlled and a second measurement replacing the reflector by a microwave-absorbing charge.

The calibration takes place by directly placing the microwave horn 20 in front of the reflector. The reflector, e.g. constituted by a metal foil is then engaged on the opposite face of the structure. This can in particular be obtained by creating a tight peripheral joint between the reflector and the structure with the aid of mastic and by forming a vacuum in the thus formed tight area between the reflector and the structure to be controlled.

The measurement in the presence of the reflector is then performed by placing the microwave horn 20 in front of the relevant area of the structure. The reflector is then removed and replaced by a foil constituting the microwave-absorbing charge. This foil is put into place in the same way as the reflector, i.e. by vacuum. The measurement in the presence of the charge is then carried out replacing the microwave horn 20 in front of the area in question.

In the case where the control or inspection relates to a repaired area of a radome, the measurements are successively performed in the presence of a reflector and a charge in said repaired area. The same measurements are then performed in another, unrepaired area of the radome having substantially the same curvature and the same surface finish as the repaired area.

Thus, the measuring device according to the invention makes it possible to carry out an inspection or control on site, without any distortion of the phase component of the signal, in accordance with the sought objective.

I claim:

1. Device for measuring the reflection coefficient of a structure exposed to microwave radiation comprising:

a first microwave radiation generator emitting a microwave radiation signal at a first given frequency, at least one combined microwave applicator-receiver which can be plated to the structure, a rigid microwave transmission line connecting the first generator to the applicator-receiver, means for measuring the amplitude and phase of the reflection coefficient, branching means placed in the transmission line and connecting the transmission line to the measuring means for transmission of a signal received at the branching means from the applicator-receiver, a second microwave radiation generator emitting a microwave radiation signal at a second given frequency, which second given frequency differs from the first given frequency by a given low frequency, first mixer means for establishing a reference signal at said low frequency, said reference signal being equal to the difference of the signals from the first and second generators, second mixer means for establishing a measuring signal at said low frequency, said measuring signals being equal to the difference of the signals from the branching means and the second generator, and wherein the first and second generators, the microwave applicator-receiver, the first and second mixer means, the branching means and the microwave transmission line form a portable device connected to the measuring means by flexible, low frequency cable.

2. Device according to claim 1, wherein the portable device also comprises:

a first power divider placed on the microwave transmission line upstream of the branching means, sampling a given power fraction of the microwave radiation signal emitted by the first generator in order to transmit it to the first mixer means and a second power divider placed on a second microwave transmission line connecting the second generator to the second mixer means and sampling the same given power fraction of the microwave radiation signal emitted by the second generator in order to transmit it to the first mixer means.

3. Device according to claim 2, wherein said given power fraction is equal to half the power of the microwave radiation signals emitted by the first and second generators.

4. Device according to claim 1, wherein the branching means comprises a circulator ensuring the transmission to the microwave applicator-receiver of the microwave radiation signal from the first generator and the transmission to the second mixer means of the microwave radiation signal reflected by the structure and intercepted by the microwave applicator-receiver, whilst preventing any other transmission.

5. Device according to claim 1, wherein the microwave applicator-receiver is directly connected to the branching means.

6. Device according to claim 1, wherein the measuring means comprises detection means, which determine the amplitude and phase of the reflection coefficient.

7. Device according to claim 6, wherein the measuring means also comprises means for recording and exploiting the amplitude and phase determined by the detection means.

* * * * *